United States Patent [19]

Nishimura et al.

[11] Patent Number: 5,761,337
[45] Date of Patent: Jun. 2, 1998

[54] METHOD AND APPARATUS FOR INSPECTION OF THE APPEARANCE OF BUMPS

[75] Inventors: Hidetoshi Nishimura, Ikoma-gun; Yuichi Shirouchi, Fukuyama, both of Japan

[73] Assignee: Sharp Kabushiki Kaisha, Osaka, Japan

[21] Appl. No.: 692,153

[22] Filed: Aug. 5, 1996

Related U.S. Application Data

[63] Continuation of Ser. No. 240,888, May 11, 1994, abandoned.

[30] Foreign Application Priority Data

May 13, 1993 [JP] Japan ................... 5-111503

[51] Int. Cl.⁶ ........................................... G06K 9/00
[52] U.S. Cl. ..................... 382/150; 382/108; 348/126
[58] Field of Search ........................ 382/149, 150, 382/151, 108; 348/109, 126; 356/237, 374, 376

[56] References Cited

U.S. PATENT DOCUMENTS

| | | | |
|---|---|---|---|
| 4,809,308 | 2/1989 | Adams et al. | 382/150 |
| 4,926,452 | 5/1990 | Baker et al. | 382/150 |
| 5,015,097 | 5/1991 | Nomoto et al. | 382/150 |
| 5,023,916 | 6/1991 | Breu | 382/150 |
| 5,058,178 | 10/1991 | Ray | 382/150 |
| 5,164,994 | 11/1992 | Bushroe | 382/150 |
| 5,166,753 | 11/1992 | Tokura | 348/126 |

FOREIGN PATENT DOCUMENTS 4-113259   4/1992   Japan.

*Primary Examiner*—Leo Boudreau
*Assistant Examiner*—Chris Kelley
*Attorney, Agent, or Firm*—Nixon & Vanderhye

[57] ABSTRACT

A semiconductor chip with bumps to be inspected is placed directly below a CCD, which captures an image of the bumps under dark field illumination. A reference window is set around each bump in the image. The reference window is enlarged or reduced or divided into subwindows such that optimal windows are provided for extraction of characteristic values of various defects. Characteristic values of particular defects are extracted from the image data within the corresponding optimal windows. The characteristic values for the bumps are statistically processed to obtain an evaluation value having a permissible range. The characteristic value of each bump is compared with the evaluation value and when the comparison indicates that the characteristic value is outside of the range, the bump is decided as a defective bump.

15 Claims, 7 Drawing Sheets

| | Sectional Views of Bumps | Images (Dark Field Illum.) | Sectional Views of Bumps | Images (Dark Field Illum.) | Kinds of Fault |
|---|---|---|---|---|---|
| Non-defective | A |  | | | |
| | B |  | | | |
| Defective | C |  | | | Connection Fault |
| | D |  | | | Short Circuit |
| | E-1 |  | E-2 |  | Connection Fault |
| | F |  | | | Connection Fault |
| | G-1 |  | G-2 |  | Connection Fault |

METHOD AND APPARATUS FOR INSPECTION OF THE APPEARANCE OF BUMPS

This is a continuation of application Ser. No. 08/240,888, filed May 11, 1994, now abandoned.

BACKGROUND OF THE INVENTION

1. Field of the Invention

The present invention relates to a method and apparatus for inspecting the appearance of bumps, which are formed at electrode portions of a semiconductor chip, to detect defective bumps during a tape carriage package die test.

2. Description of the Prior Art

A semiconductor chip bonding method using bumps formed at electrode cites of a semiconductor chip, that is, a flip chip bonding, is a good method for bonding the semiconductor chip to the surface of a circuit board such as a printed circuit board.

Such bonding of a semiconductor chip to a circuit board by means of bumps is carried out in the following way for example. First, a semiconductor chip is placed on a printed circuit board such that solder bumps on the semiconductor chip are in aligned contact with their corresponding metallized regions on the surface of the printed circuit board. Then the semiconductor chip and the printed circuit board are heated so that the solder bumps are reflowed. Thus, the electrode portions of the semiconductor chip and the metallized regions on the printed circuit board are bonded.

Reliability of the bump bond is deteriorated by missing or defective bumps created during the bump formation process. For example, if bumps are missing, or if cavities are formed in bumps by foams having mingled in the bumps during the bump formation process, or if bumps have an insufficient height due to insufficient growth of the bumps, no electrical connection is made between the bond sites of the semiconductor chip and the circuit board.

Also, if adjacent two bumps are too close in distance to each other, the two bumps will bridge during the reflow process, resulting in an undesired short-circuit.

It is common practice that these and other defects are detected by visual inspection, which is effected by using a stereomicroscope after completion of the bump formation process. However, there is a desire that the bump inspection be automated, in terms of difficulty in employment of inspectors and variation in product quality due to personal causes such as failure to find defects, inconsistent acceptance criteria, etc.

U.S. Pat. No. 5,058,178 issued Oct. 15, 1991 to Ray discloses an automated bump inspection method. According to the disclosure of the patent, the inspection is carried out by first illuminating the surface of an article having specular, three-dimensional topographical features with dark field illumination. Next, the image of the surface is captured by an image-acquisition device, such as a CCD (charge coupled device) or television camera, whose optical axis is substantially normal to the surface of the article.

Then, a first window is created around a bump presence area in the image and second windows (which are referred to as bounding boxes in the patent) are created around the individual bumps in the first window. Next, values of certain attributes associated with the first window (i.e., its location, size, and the number of the second windows therein) as well as values of certain attributes associated with each second box (i.e., its location, size and spacing from its closest neighbor) are measured. Also the values of certain attributes associated with the bright area corresponding to each bump inside each second window (i.e., its dimension, shape and brightness) are also measured. The measured values of the attributes are compared with respective reference values which represent the expected values of the attributes when no defect is present. When comparison results indicate that there is a deviation in the value of each attribute from its corresponding reference value by more than a predetermined tolerance, the bump measured is determined to be defective.

The patent also discloses that particular defects (i.e., poor wetting, squashed bumps, and near shorts) may be verified by first illuminating the surface of the article with bright field illumination instead of dark field illumination.

The above conventional inspection methods are directed to specular, three-dimensional features. Therefore, the methods are very effective in detecting defects of bumps which have a specular or mirror-like smooth surface. However, not all bumps have a specular surface, and therefore the above methods are ineffective in inspecting non-specular bumps for the following reasons.

That is, in the method using dark field illumination described above, data of the attributes or characteristics of a bump are extracted only from the image within the corresponding second window enclosing the bump and then compared directly with reference values. Accordingly, data on minute irregularities on the bump surface, which have been taken in when an image of an article having the bump was picked up by illuminating the article surface by a ring light with dark field illumination, may be treated as data indicative of defects. As a result, there are cases where even good bumps which have a slightly rough surface but can function satisfactorily may be evaluated as defective. Such an evaluation is false.

Blemishes may occur on bumps at various degrees. For example, bumps having undergone a circuit operation test have traces of the prober. Bumps are also damaged by mismanipulation of operators or during transfer of chips. However, such flaws or blemishes, which does not matter at all in the subsequent assembly process, should be determined to be good in principle. These flaws, conversely, are likely to be captured as faulty irregularities of bump surfaces and result in false data. It is a matter of course that flaws that remarkably impair the height and/or shape of bumps should be evaluated as defects.

Further, there exist different bump shapes or configurations depending on the bump formation processes. Typical shapes of bumps are of, for example, hemispherical ball type, mushroom type, and strait (rectangular prism) type. Since these differences in bump shape cause in turn differences in surface state, extraction of characteristics relating to defects from the images of the bump surface is easy in some cases, but not in other cases. In other words, in the case that the bumps have projections and depressions in their appearance, it is difficult to extract the characteristics of defects from the image of the bump surface. This difficulty in such extraction is increased by non-uniformities of bump shapes caused during the bump formation (although such non-uniformities of bump shapes do not matter if within a permissible range).

SUMMARY OF THE INVENTION

The object of the present invention is therefore to provide a method and apparatus for inspecting the appearance of bumps, which can extract characteristics of bumps related to defects without being affected by the surface conditions or shapes of the bumps so as to detect the defects as accurately as possible.

In order to achieve the above object, the present invention provides a bump appearance inspection method for inspecting appearance of bumps formed at respective pad electrodes on a semiconductor chip, comprising the steps of:

(a) illuminating a surface of the semiconductor chip with the bumps at a given angle to the surface of the semiconductor chip from all of sides of the semiconductor chip;

(b) capturing an image of the bumps;

(c) storing image data of the captured image in an image memory;

(d) recognizing positions of the bumps based on the image data stored in the image memory to obtain positional data for the bumps;

(e) setting a reference window around each bump in the image based on the positional data and the image data stored in the image memory;

(f) creating a plurality of new windows on the basis of the reference window such that characteristic values of each bump attributable to a defect can be extracted from the new windows;

(g) extracting the characteristic value of each bump from the image data within the new windows;

(h) obtaining an evaluation value for each new window through application of a statistical processing to the characteristic values of the bumps within the respective new windows, the evaluation value having a permissible range;

(i) comparing the characteristic value of each bump within each new window with the evaluation value for the new window; and (j) considering the bump to be a defective bump when the comparison result indicates that the characteristic value of the bump is outside of the permissible range of the evaluation value.

According to this method of the invention, characteristic values attributable to defects are extracted with good efficiency and specified defective bumps are detected. In addition, it is possible to detect the defects while permitting various effects or influences of the condition or state of the surface of the bumps within a certain range, so that the defective bumps are detected as correctly as possible even if the bumps have a non-specular surface.

The creating of the new windows for each bump, executed at the step (f), may be performed by reducing the reference window to a boundary between a high-brightness portion corresponding to a peripheral protruded portion of the bump and a low-brightness portion corresponding to a recess portion of the bump inside of the high-brightness portion and then dividing the reduced reference window into a plurality of subwindows in a way that allows the characteristic values in the image to be extracted from every portion of the image within the reduced reference window, and the evaluation value with the permissible range for each new window is determined based on the characteristic values extracted from the image within the subwindows located at same positions in the respective reduced reference windows for the bumps.

Thus, according to the invention, characteristic values of the bump surfaces in the low-brightness portions are extracted with accuracy, and in detecting defects, flaws such as probe traces and surface roughness, which would not necessarily cause the bumps to be defective, are permitted in a certain range.

For the purpose of detecting the defect in the recess portion of the bump while permitting effects of surface roughness and a shape of the bump within a certain range, the bump appearance inspection method of the present invention may further comprise the steps of:

selecting, as candidates for defective bump, bumps considered to be detective bumps at the step (j);

setting further subwindows within each reduced reference window, the further subwindows comprising a first subwindow formed by masking a center portion of the reduced reference window and a second subwindow occupying the center portion of the reduced reference window;

thresholding the image data within the first and second subwindows into binary image data;

extracting a first characteristic value from the binary image data within the first subwindow and a second characteristic value from the binary image data within the second window for each candidate;

calculating a characteristic value of each candidate attributable to a defect that takes place in the recess portions of the bumps, using the extracted first and second characteristic values;

obtaining an evaluation value through application of a statistical processing to the characteristic values of the candidates, the evaluation value having a permissible range;

comparing the characteristic value of each candidate with the evaluation value; and determining that the candidate is a defective bump when its characteristic value is outside of the permissible range of the evaluation value.

For the purpose of detecting an abnormal peripheral edge upheaval which tends to take place to a plurality of bumps simultaneously due to a current density abnormality during bump formation, the bump appearance inspection method may comprise the steps of:

calculating an average value of the obtained characteristic values of the candidates;

comparing the calculated average value with a predetermined evaluation value; and deciding, when the average value exceeds the evaluation value, that a plurality of bumps are defective.

Furthermore, in order to detect a defective recess which may take place in a peripheral portion of the bump, the bump inspection method of the present invention may comprise the steps of:

selecting, as candidates for defective bump, bumps considered to be detective bumps at the step (j);

thresholding the image data of each candidate within its reduced reference window into binary image data and extracting the low-brightness portion from the image based on the binary image data to obtain an outline of the low-brightness portion;

calculating a characteristic value indicative of a shape of the low-bright portion based on the outline obtained;

comparing the calculated characteristic value with a predetermined evaluation value; and deciding, when the characteristic value exceeds the evaluation value, that the candidate is a defective bump.

Furthermore, in order to detect an abnormal shape of the bumps, the bump inspection method of the present invention may comprise the steps of:

selecting, as candidates for defective bump, bumps considered to be detective bumps at the step (j);

enlarging the reference window for each candidate at a given specified magnification;

thresholding the image data of each candidate within the enlarged reference window into binary image data;

extracting the high-brightness portion corresponding to the peripheral portion of the candidate from the binary image data to obtain an outline of the high-brightness portion;

calculating a characteristic value indicative of a shape of the high-bright portion based on the outline obtained;

comparing the calculated characteristic value with a predetermined evaluation value; and deciding, when the characteristic value exceeds the evaluation value, that the candidate is a defective bump.

Furthermore, in order to detect defects in the height of the bumps, the bump appearance inspection method of the present invention may comprise the steps of:

thresholding image data of each bump within the reference window into binary image data;

determining a width of each bump based on the binary image data;

calculating a height of the bump based on the width of the bump; and calculating an evaluation value with a permissible range through application of a statistical processing to the heights of the bumps;

comparing the height of each bump with the evaluation value; and determining that the bump is defective with respect to its height when a value of the height is outside of the range of the evaluation value.

According to the present invention, by combining the above steps appropriately, various kinds of defects of the bumps such as an insufficient height of the bumps, an abnormal recess, an abnormal peripheral edge upheaval, an abnormal shape of the bumps, etc., can be detected.

The method of the present invention can be carried out using an apparatus, comprising:

support means for supporting a semiconductor chip with bumps formed at its respective pad electrode sites;

image capture means for capturing an image of the bumps;

drive means for moving the support means such that the bumps of the semiconductor chip on the support means are positioned directly below the image capture means;

illumination means for illuminating a surface of the semiconductor chip with the bumps at a given angle to the surface of the semiconductor chip from its entire periphery;

storage means for storing image data of the image of the bumps captured by the capture means;

reference window setting means for setting a reference window around each bump in the image based on the image data stored in the storage means;

modifying means for modifying the reference window to create new windows according to a surface state of the bump so that characteristic values of the bumps attributable to a defect can be accurately extracted;

extraction means for extracting the characteristic values of the bumps attributable to the defect from the image data within the new windows;

calculation means for calculating an evaluation value having a permissible range through application of a statistical processing to the characteristic values of the bumps extracted by the extraction means; and defect discrimination means for comparing the characteristic value of each bump with the calculated evaluation value and discriminating based on the comparison result whether the bump is defective or not, the defect discrimination means deciding that the bump is a defective bump when its characteristic value is outside of the permissible range.

This apparatus operates as follows. First, the support means carrying one or more semiconductor chips thereon is driven by the drive means, so that the bumps on a semiconductor chip are moved to a position just below the image capture means. In this state, by the illumination means, the surface of the semiconductor chip, and hence surfaces of the bumps on the semiconductor chip, are illuminated at a specified angle to the surface of the chip from all of its sides.

Then, an image of the plurality of bumps are captured by the capture means and image data thus obtained are stored in the storage means. Subsequently, based on these image data stored in the storage means, the reference window setting means set reference widows in a specified way around the individual bumps in the image. Moreover, the modifying means modify the reference window so as to create the new windows depending on the surface state of the bumps. Then the characteristic values of the bumps related to a specific defect are extracted from the image data within the new windows by the extraction means.

After the characteristic values of the plurality of bumps are extracted, the evaluation value calculation means apply a given statistical processing to the extracted characteristic values to eventually obtain an evaluation value with a permissible range. Then, the defect discrimination means compare the individual characteristic values with the evaluation value and decide that a bump presenting a characteristic value falling outside the permissible range is defective.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

The present invention is now described in detail with reference to an embodiment thereof as shown in the accompanying drawings.

Figure 1:
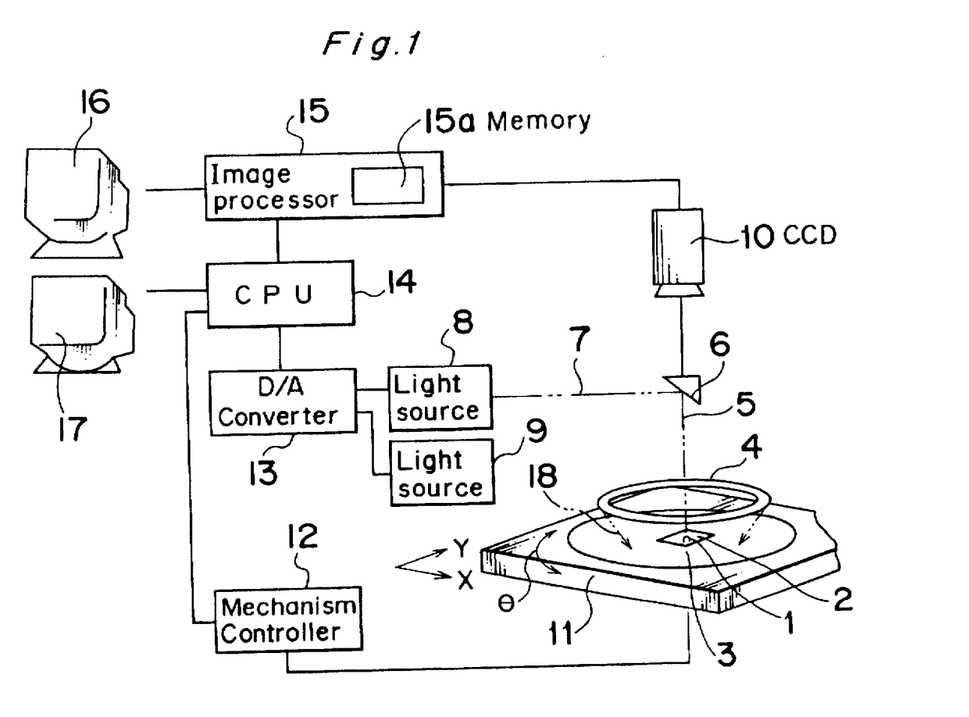
FIG. 1 is a block diagram of a bump inspection apparatus of the present invention.

FIG. 1 is a block diagram of the bump inspection apparatus for inspecting the appearance of bumps according to the present embodiment. This bump inspection apparatus has a stage 11 (movable in X-, Y-, and θ-directions) for supporting a wafer 3. The wafer 3 is transported to and from the stage 11 by a known suitable transportation device (not shown).

The stage 11 is movable in X and Y directions by two motors (not shown) which are driven by a mechanism controller 12.

A CCD (Charge Coupled Device) 10, which is an image pickup device, is installed upward of the stage 11 so that its optical axis 5 is normal to the surface of the wafer 3 placed on the stage 11.

Besides, a beam splitter 6 is provided at a point on the optical axis 5 of the CCD 10 between the CCD 10 and the stage 11. A light source 8 is positioned in a direction perpendicular to the optical axis 5 of the CCD 10 from the beam splitter 6. A generally collimated light beam 7 issued from the light source 8 enters the beam splitter 6 at a right angle to the optical axis 5 of the CCD 10, and is reflected by the beam splitter 6 toward the wafer 3. Then the collimated light beam 7 directed toward the wafer 3 coaxially with the optical axis 5 of the CCD 10 strikes the surface of the wafer 3 vertically, so that it is reflected and refracted by the surface of the wafer 3.

A ring light 4 is provided just above the wafer 3 so as to surround the optical axis 5 of the CCD 10. The ring light 4 is associated with a light source 9. The ring light 4 surrounds the wafer 3 and illuminates the surface of the wafer 3 with dark field illumination with beams 18 incident on the surface of the wafer 3 at an angle to the surface from all sides thereof. On the other hand, the light beam from the light source 8 illuminates the surface of the wafer 3 with bright field illumination.

An output signal from the CCD 10 is taken into an image processor 15 and stored in a memory 15a provided in the image processor 15. Image data relating to the surface of the wafer 3 stored in the memory 15a are subjected to various types of image processing, whereby characteristic values of the image are extracted. The extracted characteristic values are provided to a CPU (central processing unit) 14 and processed by the CPU 14. By this processing, it is determined whether a bump 1 of a chip 2 formed on the wafer 3 is defective or not.

The CPU 14 operates as a discrimination unit for discriminating whether the bump 1 is defective or not based on the extracted characteristic values supplied from the image processor 15. Moreover, the CPU 14 operates also as a main controller which controls the mechanism controller 12 to drive and control the stage 11 and which further controls the light source 8 and the light source 9 through a D/A (digital-to-analog) converter 13 to switch the illumination mode between dark field illumination and bright field illumination. To control the light sources, the CPU outputs a light-source control signal to the D/A converter 13.

The processing operation of the CPU 14 is monitored by a monitor 17. On the other hand, the operation of the image processor 15 is monitored by a monitor 16.

The image processor 15 serves as the reference window setting means, the modifying means for modifying the reference window to create new windows, and the extraction means for extracting characteristic values in the image of bumps. The CPU 14 serves as the evaluation value calculation means and the defect discrimination means for discriminating whether the bumps are defective or not.

Figure 2:
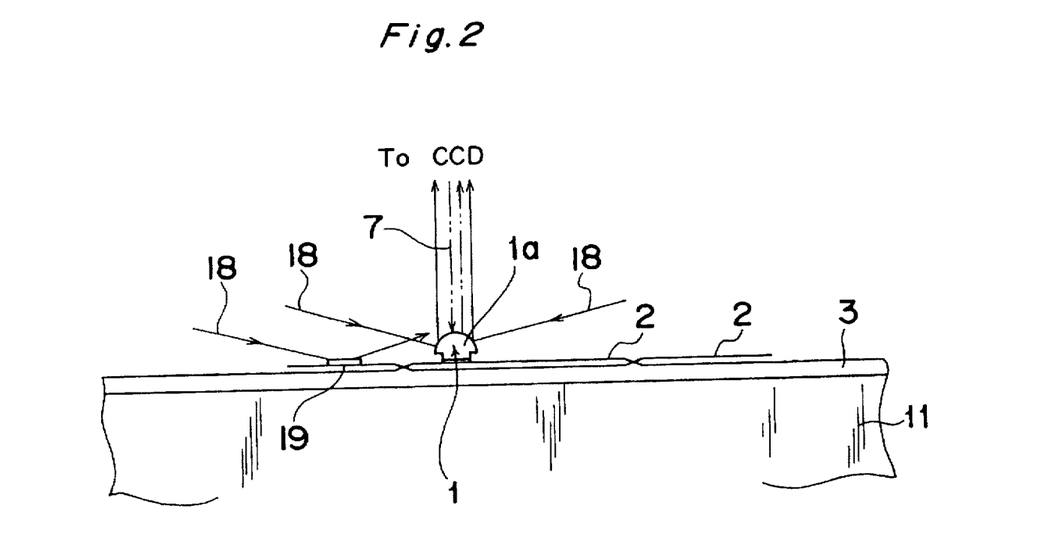
FIG. 2 is an enlarged side view of the vicinity of a wafer in FIG. 1.

FIG. 2 is an enlarged side view of the wafer 3 and its vicinities in FIG. 1. Now the bright field illumination and the dark field illumination are described with reference to FIG. 2.

In the dark field illumination, the surface of the chip 2 is illuminated with a set of beams 18 from the ring light 4. The beams 18 are directed at an angle to the surface of the chip 2 in the form of a cone, as illustrated. In this illumination, beams 18 that have struck a round, three-dimensional, curved protrusion 1a of a mushroom type bump 1 are reflected perpendicularly to the surface of the chip 2 by the protrusion 1a and enter the CCD 10. On the other hand, beams 18 that have struck a non-upheaved, flat surface such as a metal pad 19 formed on the chip 2 are regularly reflected, and thus will not enter the CCD 10.

Thus, with dark field illumination, image data can be obtained on the protruded portion upheaving upward and curving from side wall toward top wall.

On the other hand, in the bright field illumination, the surface of the chip 2 is illuminated with the generally collimated light beam 7 normal to the surface, which have been projected from the light source 8 and reflected by the beam splitter 6. With this illumination, a collimated light beam 7 that has struck a flat portion of the bump 1 is reflected perpendicularly to the surface of the chip and enters the CCD 10. A collimated light beam 7 that has struck the curved portion of the bump 1 will not enter the CCD 10.

Thus, image data on a flat surface of the bump 1 parallel to the stage 11 can be obtained by the bright field illumination.

Figure 3:
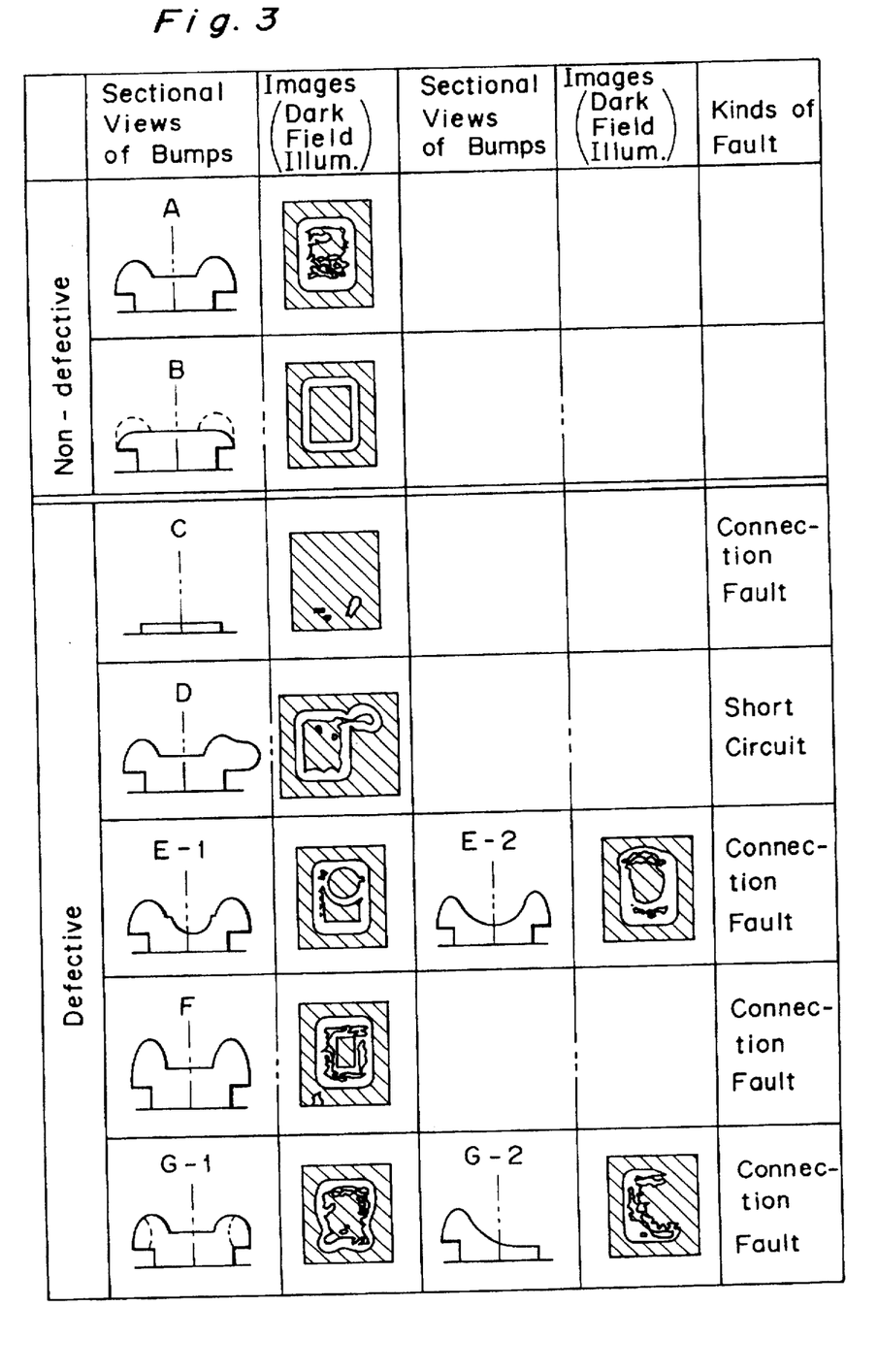
FIG. 3 is a view showing examples of images of defective and non-defective bumps taken under the dark field illumination condition.

FIG. 3 shows images of defective bumps having various defects and those of good (non-defective) bumps obtained with dark field illumination. In FIG. 3, a hatched portion represents a dark portion of the image and a non-hatched portion represents a bright portion of the image.

As seen in FIG. 3, images of good bumps "A", "B" obtained by the CCD 10 each have a generally rectangular bright loop with the center portion being dark. As understood from the sectional views of the bumps shown in FIG. 3 and from FIG. 2, the bright rectangular loops are observed due to the upheavals on the periphery of the bumps illuminated from the whole circumference by the ring light 4.

Various methods are conceivable as a method of extracting the quantities or values of attributes, i.e., characteristic values of the bumps in order to detect defects as listed in FIG. 3. One effective method is to extract the characteristic values after dividing the bump image into a bright portion (hereinafter, referred to as a high-brightness portion) on the periphery and a dark portion (hereinafter, referred to as a low-brightness portion) inside the high-brightness portion by means of windows. Dividing the surface image of the bump 1 by means of windows in this way allows various defects to be classified into peripheral abnormalities and central abnormalities.

Further, for extraction of the characteristic values of the bump, bright portions resulting from reflection by surface irregularities are targeted. Accordingly, the high-brightness portion in the periphery of the bump image, which portion varies with surface roughness and its formation state, is excluded from the inspection by a window. This ensures stable extraction of the characteristic values of the bumps.

Figure 4:
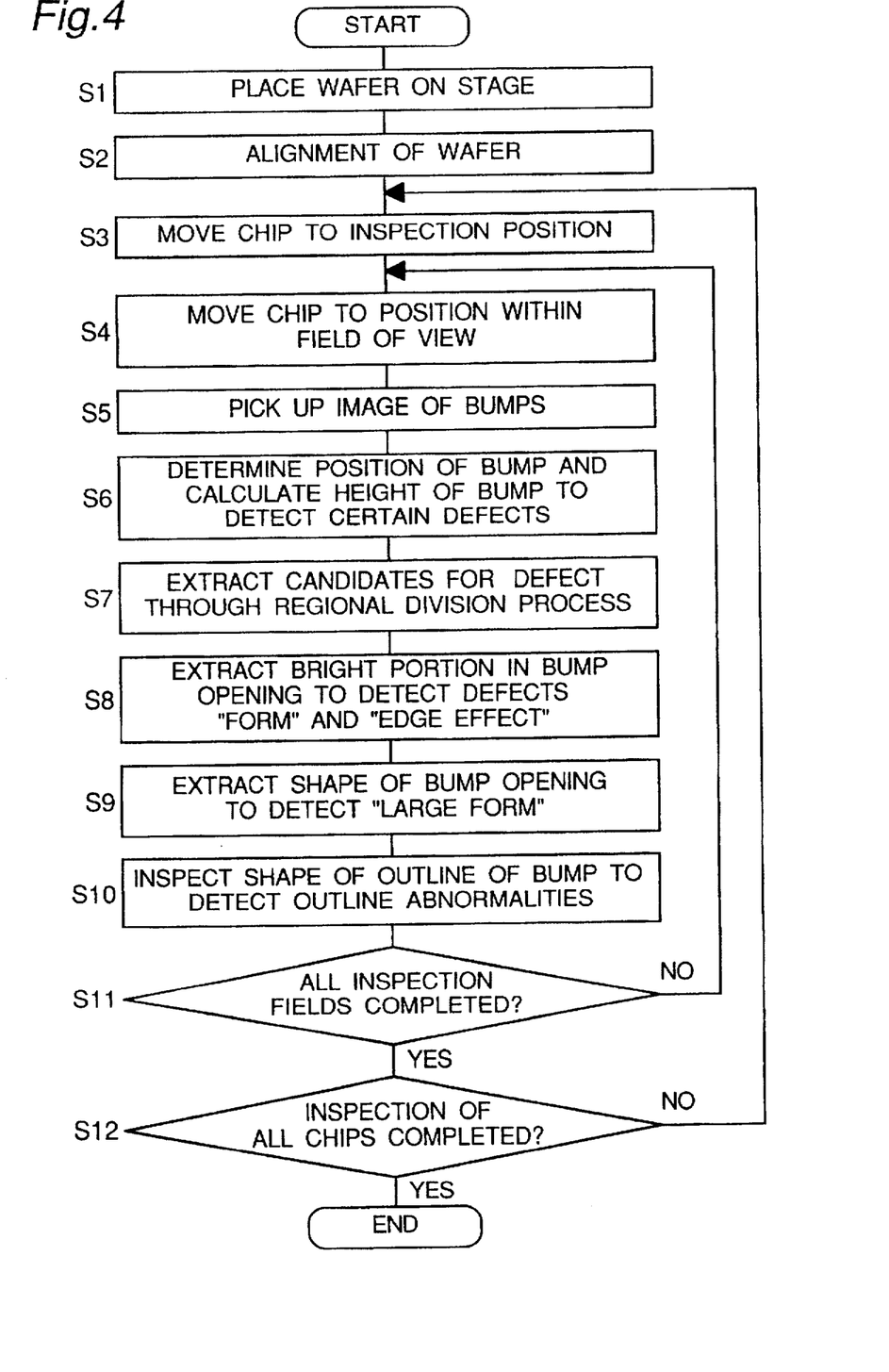
FIG. 4 is a flow chart of the processing performed by the image processor and CPU in FIG. 1 for inspection of bumps.

FIG. 4 is a flow chart of the program performed by the image processor 15 and the CPU 14 in inspecting the appearance of the bumps 1 on the wafer 3. Here is described the operation of the bump inspection process with reference to FIG. 4.

It is noted that, when starting the operation of the bump inspection process, data on the size of the wafer 3, the size of the chip 2, and the position of a good bump have been previously registered in the memory 15a in the image processor 15.

At step S1, the wafer 3 is placed on the stage 11 by a transportation system of any known type.

At step S2, alignment of the wafer 3 is carried out. When an image processing technique is utilized, the alignment is carried out as follows. First, the ring light 4 is turned out, and the surface of the wafer 3 is illuminated by the light beam from the light source 8 with bright field illumination. In this state, the position of the center of the wafer is calculated in the following manner. First, coordinates of three points on the sides of the wafer 3 are calculated. Next, coordinates of the intersection point of bisectors of line segments that connect every two points of the three points are calculated within the registered wafer size, whereby the center position of the wafer 3 is recognized. Then an orientation flat is recognized from the center of the wafer 3. Thus, alignment among the X-axis, the Y-axis, and the wafer 3 is accomplished.

At step S3, a chip 2, which is an inspection target, that is, an object of the inspection, is moved to the inspection position.

At step S4, the chip 2 is further moved to the inspection field position.

In doing this, if the chip 2 is too large to be fully included within the field of view by a single intake of image data, the image of the chip 2 is divided beforehand into a plurality of regions according to the field size based on the chip size previously registered.

At step S5, the light source 8 is turned out, and the surface of the chip 2 is illuminated by the ring light 4 with dark field illumination. Then the mechanism controller 12 is controlled by the CPU 14 to move the stage 11 so that a specified number of bumps are positioned directly under the CCD 10. In this state, an image of the bumps 1 is picked up or captured by the CCD 10.

At step S6, the positions of the bumps 1 are predicted based on the registered positions of good bumps, and reference windows are formed that mask regions of the picked-up image other than regions surrounding the bumps. Then, image data within the reference windows are thresholded into binary image data, and pixels of upheaved portions (high-brightness portions) on the periphery of the bumps are extracted. Thereafter, the extracted pixels are projected onto the X- and Y-axis, whereby coordinates of the positions of the bumps are recognized.

The coordinates of the position of the bump 1 obtained in this way are compared with the registered coordinates of the position of a good bump to find whether the bump is absent (missing) or not (the bump C in FIG. 3 is missing). Also, from the above obtained coordinates of the position of the bump, defects causing a spacing abnormality ("D" in FIG. 3) and an abnormal height of the bump are detected.

At step S7, candidates for defective bump are selected through a regional division process as described later in detail.

At step S8, as will be detailed later, image data on the surface of each candidate for defective bump selected at step S7 is subjected to optimum thresholding, a window which encloses a recess portion (hereinafter, referred to as an opening) inside the peripheral protruded portion of the bump 1 is formed, and a bright portion in the opening (i.e. a rather bright portion in the low-brightness portion) is extracted. Then, based on the binary image data of the extracted bright portion, the characteristic values of the bright portion in the opening of the image data are quantitatively determined.

By using these quantitatively determined characteristics, a defect that a large cave-in or depression is developed in the surface by foams having mingled in the bump during the bump formation process (hereinafter, the defect is referred to as "foam"), such as exemplified by "E-1" in FIG. 3, is recognized. Further, another defect that the bump periphery is abnormally protruded due to excessive current densities at the bump location (hereinafter, the defect is referred to as "edge effect"), such as exemplified by "F" in FIG. 3, is recognized.

At step S9, characteristic values representing the shape of the bump opening are extracted, whereby a foam that could not be extracted at step S8 (hereinafter, referred to as "large foam"), such as exemplified by "E-2", are recognized.

Since such a defect, "large foam", ranges up to the bump periphery, values representative of such a large foam cannot be extracted within the window set at step S8. Accordingly, there arises a need for another method as will be detailed later.

At step S10, outline shapes of bump images are inspected in a way detailed later such that any outline abnormalities of bump surfaces as exemplified by "G-1" and "G-2" in FIG. 3 are recognized.

At step S11, it is determined whether or not the processing has been completed for every individual inspection-target region (hereinafter, referred to as inspection view field) obtained by dividing the image according to the field size of one chip 2. If the processing (steps S4–S10) for every inspection view field has not been completed, the processing returns to step S4, where processing for the next inspection view field of the same chip 2 succeeds. On the other hand, if the processing for every inspection view field has been completed, the program goes to step S12.

At step S12, it is discriminated whether or not the processing for all the inspection-target chips 2 in the wafer 3 is completed. If it has not been completed, the program returns to step S3, where processing for the next chip 2 is started. On the other hand, if the processing for all the inspection-target chips 2 has been completed, the operation of bump appearance inspection processing is terminated.

Next described in detail are the calculation of the height of the bump, executed at step S6, the selection of candidates for defective bump through the regional division process, executed at step S7, the recognition of "foam" through quantitative determination of characteristics of the bump opening, executed at step S8, recognition of "large form", executed at step S9, and the inspection of the shape of the outline of the bump, executed at step S10, in connection with the flow chart of the bump appearance inspection processing.

(1) Calculation of the height of the bump

Figure 5A:
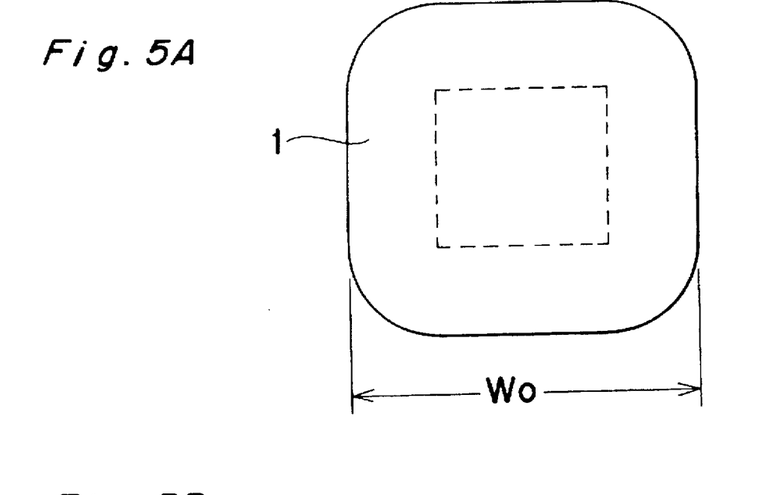
FIGS. 5A and 5B are a top view and a sectional view of a bump.
Figure 5B:
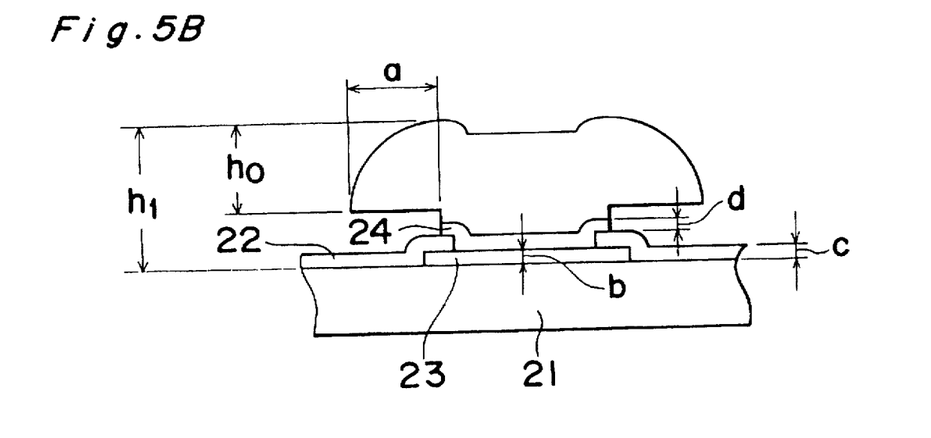
Figure 6:
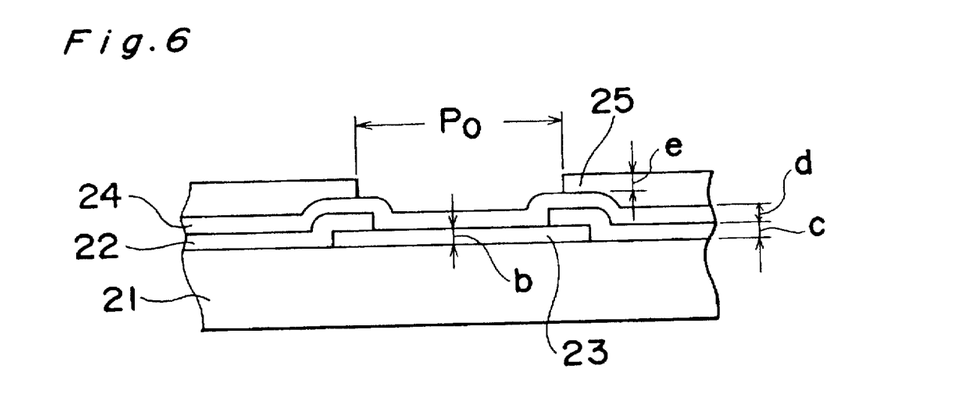
FIG. 6 is a sectional view of a pad electrode site of a semiconductor substrate to which the bump as shown in FIG. 5 is formed.

First, the calculation of the height of the bump, executed at step S6, is described in detail with reference to FIGS. 5A, 5B and 6. FIG. 5A shows a top view of a bump 1, FIG. 5B shows a sectional view of the bump 1 formed at a pad electrode site of a semiconductor chip, and FIG. 6 shows a sectional view of the pad electrode and its vicinity of the semiconductor chip prior to bump formation, wherein reference numeral 21 indicates a semiconductor substrate, reference numeral 22 indicates a semiconductor protection film, reference numeral 23 indicates the pad electrode, reference numeral 24 indicates a metal film and reference numeral 25 indicates a photoresist.

The height of the bump 1 is calculated by making use of the value of width of the bump 1.

Figure 7:
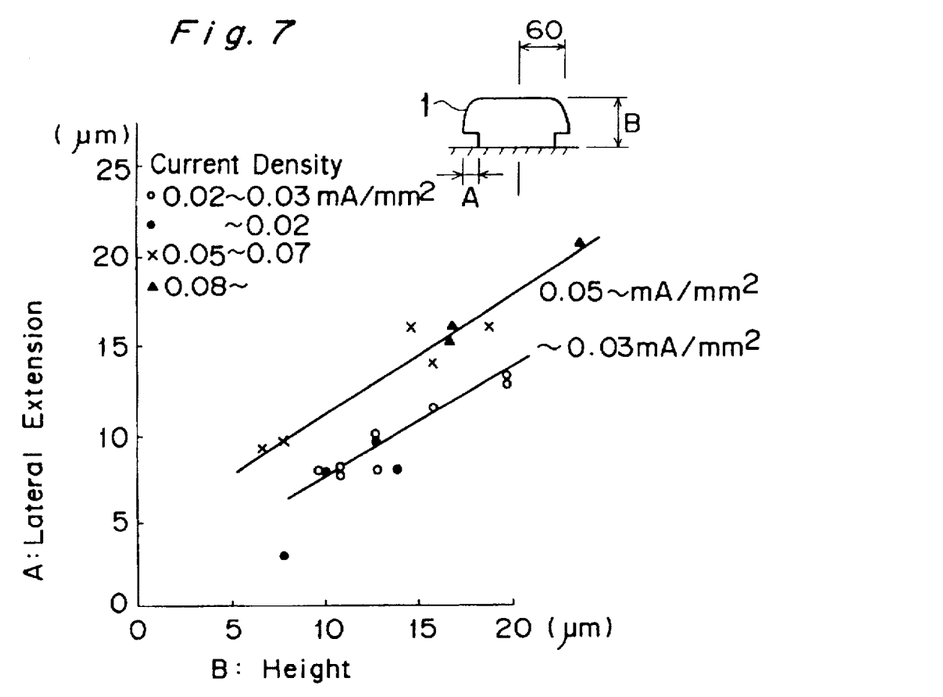
FIG. 7 is a chart showing the relation between the lateral extension of the bump and the height of the bump.

Ordinarily, as shown in FIG. 7, a proportional relation holds between a lateral extension A of the bump 1 (width of the eaves of the bump 1) and its height B (see the Japanese literature entitled "An introduction to TAB Technique", Kenzo Hatada). Accordingly, first a relation between the lateral extension A of the bumps and their height B is obtained through experiments or the like. Then, by using a lateral extension "a" calculated from a bump width "$W_0$" in FIG. 5A and a bump pattern size "$P_0$" in FIG. 6, a height growth amount ho developed over the photoresist 25 is calculated from the obtained relation between the lateral extension A and the height B.

Next, a height "$h_1$" from the semiconductor substrate 21 is calculated using the above-calculated height growth amount "$h_0$" developed over the photoresist 25 (i.e., height of the bump above the level of the semiconductor substrate), the thickness "b" of the pad electrode 23 obtained by measurement prior to the bump electrode formation, the thickness "c" of the semiconductor protective film 22, the thickness "d" of the metal film 24, and the thickness "e" of the photoresist 25.

Figure 8:
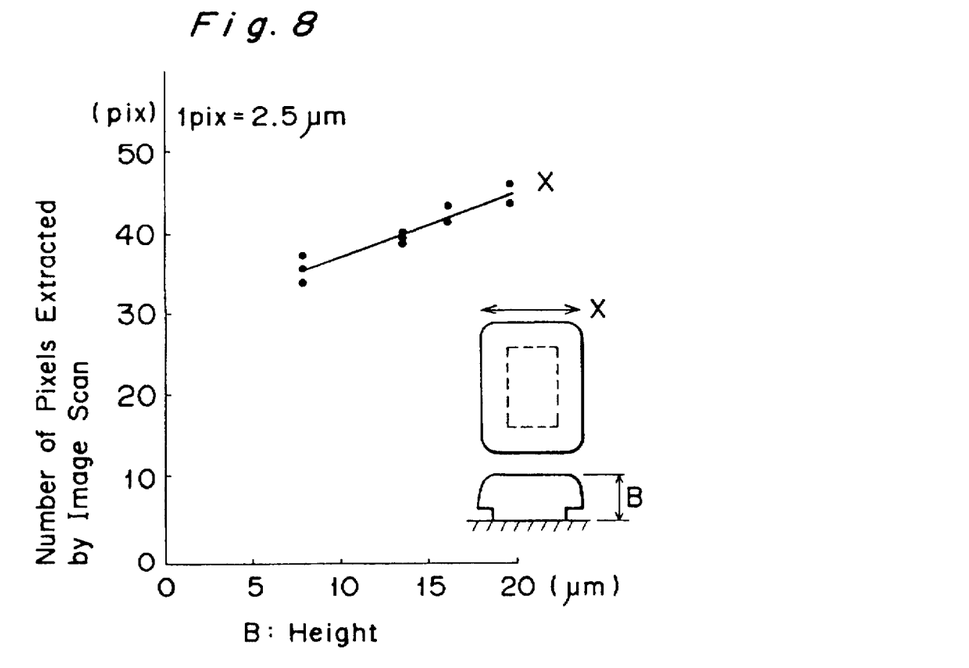
FIG. 8 is a chart showing the relation between the width and height of the bump.

FIG. 8 gives values of the bump width X and the height B actually measured from sample images. The figure establishes that the bump height B is proportional to the bump width X. That is, the bump height can be determined on the basis of the bump width determined from image data of the bump 1.

(2) Selection of candidates for defective bump through regional division process Next, the regional division process in selecting candidates for defective bump, executed at step S7, is described in detail with reference to FIGS. 9A–9F that show an example of regional division which allows extraction of the characteristic values of the image in the entire opening of the bump 1.

It is probe traces that matter in extracting characteristic values of defects from the bump 1 having undergone the circuit operation test. The degree to which the probe traces are impressed on the surface of the bump 1 depends on the contact condition between the prober and the bump 1. The probe traces can affect values of certain attributes of the image. For example, in extracting the values of the "black" characteristic to a defect, probe traces also might be recognized as a defect because the probe traces are black and moreover their shapes and positions cannot be distinguished.

Thus, there arises a need for the method that allows it to be discriminated whether or not any defects are present while permitting the probe traces.

In this embodiment, presence of defects is determined while flaws or surface roughness such as probe traces is permitted within a certain range, by taking advantage of the fact that adjacent bumps 1 have a similarity in surface characteristics (For example, there is a great possibility that a bump adjacent to a good bump that presents particular probe traces may be a good bump on which similar probe traces are impressed.) That is, by first gathering the values of certain characteristics of the images of the various bumps and then statistically processing the values to obtain an evaluation value, determination on the presence of defects is made using the evaluation value.

Now it is assumed that averages of image densities of images of the surfaces of the bumps 1 and standard deviations of image density are used as the characteristic values. It is noted that the average value of image density and the standard deviation are indexes showing a contrast in the surface. In this connection, if an average value of image density and a value of standard deviation are calculated and used as characteristic values without being subject to any processing, discrimination cannot be made between defects and mottled patterns, so that rough bump surfaces would rise a problem. Accordingly, in such a case, there is a need of filtering image data by the image processor 15 in order to make the image previously blurred.

Minute variations cannot be captured if the characteristic values of the image of the bump 1 are extracted from one window which is created by modifying the reference window so as to surround the low-brightness portion in the image. Thus, in this embodiment, the window (shown by a broken line in FIG. 9A) is further divided.

However, merely dividing the window into a lattice-like shape would make it impossible to extract characteristic values under the divisional lines. Therefore, in this embodiment, the window is divided as shown in FIGS. 9B–9F.

Figure 9A:
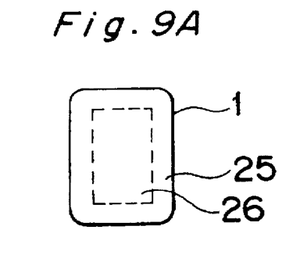
FIG. 9A illustrates a window used in measuring characteristic values of bumps in accordance with the present invention.
Figure 9B:
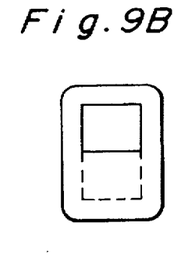
FIGS. 9B–9F illustrate subwindows obtained by dividing the window of FIG. 9A, the subwindows being optimum for extracting characteristics of defects.
Figure 9C:
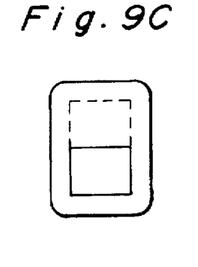
Figure 9D:
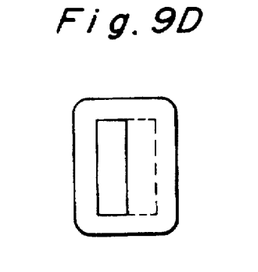
Figure 9E:
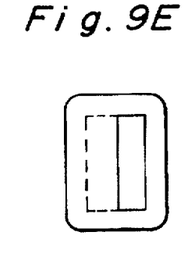
Figure 9F:
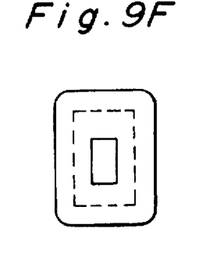

More specifically, the window shown in FIG. 9A is divided into five subwindows. Four of the subwindows shown in FIGS. 9B, 9C, 9D, and 9E each correspond to one of the two regions resulting from longitudinally or laterally dividing the window (FIG. 9A) that is set on the boundary between the high-brightness portion 25 on the periphery of the image of the bump 1 surface and its inner low-brightness portion 26, and the other subwindow shown in FIG. 9F is set in a center region of the window of FIG. 9A.

By extracting characteristic values of the image with the five subwindows overlapped with one another, the values even below the divisional lines can be extracted securely, so that the characteristic values are extracted from the thorough region of the image surrounded by the window of FIG. 9A.

In order that defects can be recognized while probe traces are permitted, as described above, in this embodiment, candidates for defective bump are selected through comparison between the characteristic value and the evaluation value obtained by gathering the characteristic values extracted from the subwindows shown in FIGS. 9B–9F and subjecting them to a statistical processing.

Now, n characteristic values extracted from n bump images present within the inspection field using one of the subwindows shown in FIGS. 9B–9F are assumed to be a, b, c, d, and e. Then the evaluation value having a given permissible range for the characteristic values for the subwindow is determined from the following equations (1) to (3):

$$\text{Average } \bar{X}_i = (a + b + c + d + e)/n \quad (1)$$

$$\text{Dispersion } SD = \sum_{i=1}^{n} (X_i - \bar{X}_i)^2 \quad (2)$$

$$\text{Evaluation value } (+ \ldots \text{ upper limit } - \ldots \text{ lower limit}) = \quad (3)$$

$$\bar{X}_i \pm 3.0 * SD/\sqrt{n}$$

Any characteristic value deviated out of the evaluation value range is regarded as representing a candidate for defective bump.

The above calculation method for the evaluation values can be applied to cases where characteristic values are of normal distribution.

According to the above-described regional division process, the evaluation values can be obtained from a large number of bump images for each of the subwindows. This makes it possible to permit variation in the characteristic values in good bumps by taking advantage of the similarity in adjacent bumps. Further, by recognizing characteristic values deviated out of the evaluation value range as candidates for defects, it is possible to decrease false data due to probe traces, surface roughness of the bumps 1, or other factors in the process of sorting various defects or flaws, which process will be involved later.

(3) Recognition of "foam" through quantitative determination of characteristic values of the opening Next described is the quantitative determination of characteristics based on binary image data of the bump opening, carried out at step S8.

The above-mentioned "foam", i.e., a defective depression or recess on the bump surface (see E-1 in FIG. 3), may take place anywhere of the bump 1 surface. Further, depressions of such degrees that electrical connection can be obtained thereacross are not defects. Whether or not electrical connection can be obtained depends on the height or depth of the bump 1. The depth of the bump can be estimated from the size of a mouth portion of the foam or depression, because of its spherical shape. Thus, the defect "foam" can be determined on the basis of the presence/absence and size of the mouth portion of the depression.

The mouth portion of the "foam" can be recognized from characteristic values within the opening of the bump 1. Therefore, setting a window at the opening of the bump 1 and extracting values of a bright portion representing the mouth portion of the foam allows the size of the foam to be recognized.

In doing this, it is important to set an optimum window. More specifically, too small a window could not offer sufficient data. Conversely, too large a window would result in extraction of values of the high-brightness portion as well, which is the protruding portion on the periphery of the bump 1, so that the bump peripheral portion and the mouth portion of the foam, both being bright portions could not be discriminated from each other.

Figure 10A:
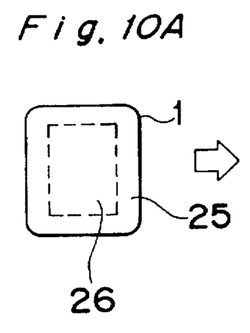
FIG. 10A illustrates a window.

For the above reasons, in this embodiment two windows (a first window 27 and a second window 29) are formed on the basis of a window (a reduced reference window) shown by a broken line in FIG. 10A that is equal to the window shown in FIG. 9A. As described above in connection with FIG. 9A, the window is formed on the boundary of the outer, high-brightness portion 25 and the inner, low-brightness portion 26.

Figure 10B:
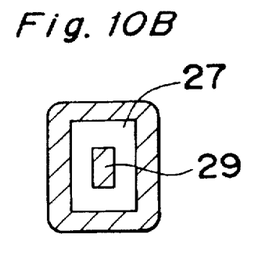
FIGS. 10B and 10C illustrate example of windows optimum for extracting a bright portion in the opening of the bump.
Figure 10C:
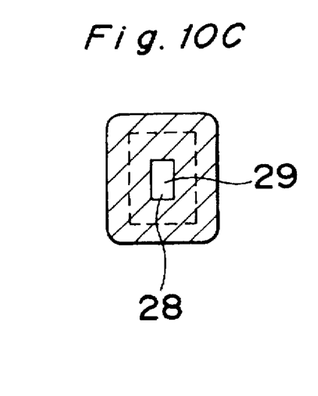

The first window 27, shown in FIG. 10B, is equivalent to the window of FIG. 10A without its center region 29 (that is, the center region of the image in the window of FIG. 10A is masked), and the second window 28, shown in FIG. 10C, surrounds the center region 29.

Then, the image data of the bump 1 surface is binarized for each of the first window 27 and the second window 28, and high-brightness pixels are extracted from the resulting binary image data, where the number of extracted pixels is taken as the characteristic value. In this process, although bright portions due to surface roughness of the bump 1 also are included in extracted data representing the defect, "foam", such data relating to the surface roughness can be decreased by suitably setting the threshold in converting the image data into binary data, to such a degree that defect discrimination is not thereby affected.

Rather, it is problematic that data on the protrusions projecting inward from the upheavals on the periphery of the bump 1 are contained in the values extracted from the first window 27.

For this reason, in this embodiment, both a first characteristic value extracted from the first window 27 and a second characteristic value extracted from the second window 28 are weighted, whereby unnecessary effects of the first characteristic value are suppressed. In this way, a characteristic function f optimum for detection of faulty "foam" is obtained:

Characteristic function f=first characteristic value/A+second characteristic value * B where A and B are constants.

The constants A and B are given by optimum values selected from characteristic values indicative of the defect of a large number of samples.

Constants A and B were determined in this embodiment as follows.

First, respective characteristic values attributable to the defect were given to a large number of sample good bumps and sample defective bumps having the defect "foam" through functional inspection. Next, the first characteristic value and the second characteristic value were obtained from image data of the samples. Then, constants A and B were determined optimally from both the characteristic value of the defect and the first and second characteristic values. As a result, optimum values A=20.0 and B=1.5 were obtained.

With the function f using the constants A and B obtained as optimum values in this way, characteristic values are calculated from the first and second characteristic values in the n bump images present within the inspection field. Then, the n characteristic values calculated are statistically processed by equations (1) through (3) above to determine an evaluation value, and faulty "foams" are recognized based on the determined evaluation value. As a result, effects of the upheavals on the periphery of the bump 1 and effects of the formation state of the bump 1 (inward protrusion, etc.) can be relieved or decreased.

The above-mentioned defect "edge effect" (F in FIG. 3) takes place to a plurality of bumps at the same time for the following reason. That is, the bumps 1 grow in proportion to the density of an electric current applied for formation of the bumps, while generated defects are also affected by the density of the current. Further, since the bumps are formed in batch processing, defective bumps will take place not singly but in a group.

On the other hand, in the "edge effect", the periphery of the bump 1 abnormally protrudes as illustrated in (F) in FIG. 3, so that the rectangular opening on the bump 1 surface (the low-brightness portion 26 in FIG. 10A) is narrowed inward of the bump 1. If the edge of the opening is present within the first window 27 shown in FIG. 10B, the edge is recognizable by the method using the aforementioned function f.

Accordingly, the defect "edge effect" is defected in the following manner in this embodiment. Characteristic values of the candidates for defects are calculated by the function f, an average value of the calculated characteristic values is calculated, and the average value is compared with an evaluation value previously set. If the average value is higher than the evaluation value, it is recognized that the defect has taken place to a plurality of bumps. In this way, a discrimination of the defect "edge effect" is made.

(4) Recognition of the "large foam"

Next described is the recognition of the large foam, executed at step S9.

In recognition of the defect "large foam" (the bump E-2 in FIG. 3), first the image data of the candidates for defective bump selected at step S7 are thresholded into binary image data for extraction of the low-brightness portion. In this process, since characteristics of the low-brightness portion are an object of the inspection, there is a need of previously eliminating any effects of the probe traces from the binary image data of the low-brightness portion. It is noted that in this embodiment any effects of probe traces have already been eliminated by the regional division process executed at step S7.

Then an outline of the low-brightness portion is determined from the binary image data of the low-brightness portion, and based on the outline of the low-brightness portion, values characteristic to the defect are determined.

However, the characteristic values extracted based on the outline of the low-brightness portion include those of the good bumps "B" in FIG. 3. Therefore, the defective bumps "E-2 (large foam)" cannot be distinguished from the good bumps "B" in FIG. 3. Thus, in order to make the good bumps "B" in FIG. 3 distinguishable from the defective bumps, the following shape value is applied.

That is, the difference in image between the defective bump "E-2 (large foam)" and the good bump "B" in FIG. 3 is that the outer edge of the low-brightness portion in "E-2 (large foam)" is rather rounded. Therefore, a "degree of circle" representing the degree of roundness expressed by the following equation (4) is set as the shape value:

$$\text{Degree of circle} = 4\pi \times (\text{area})/(\text{perimeter})^2 \qquad (4)$$

Then, the area and perimeter of the low-brightness portion are determined from coordinates of the pixels on the outline of the low-brightness portion of the defective bump "E-2 (large foam)" and of the good bump "B" in FIG. 3. A value of the "degree of circle" resulting from substitution of the determined area and perimeter in equation (4) is taken as the characteristic value of the defect "large foam". Then the determined characteristic value is compared with an evaluation value previously set, whereby the defect "large foam" is recognized.

(5) Inspection of the outline shape of the bump Next described is the inspection of the outline shape of the bump, executed at step S10.

In this step S10, first the reference window surrounding the bump 1 is enlarged by a specified magnification, so that an enlarged window that is optimum for extraction of the outline of the bump 1 is newly set. The basic position for setting the enlarged window is the coordinates of the bump position obtained at step S6.

Figure 11A:
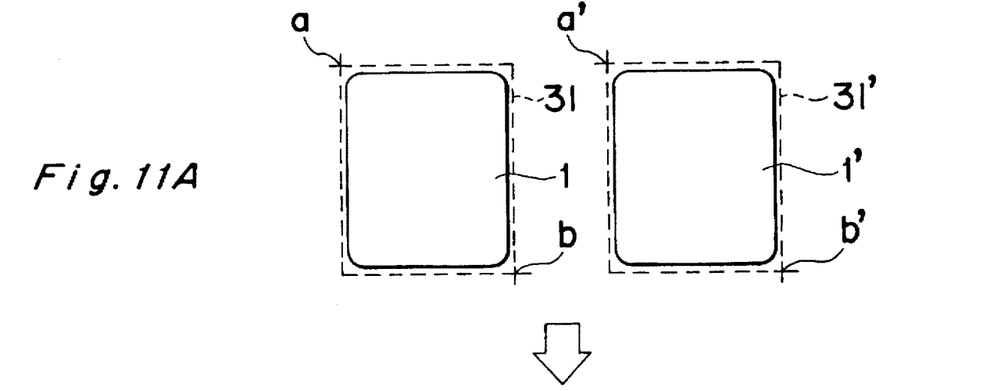
FIG. 11A illustrates reference windows set around adjacent bumps.

Setting of the enlarged window is carried out in the following way. First, based on the basic position of the bump 1 (1'), coordinates of the corners "a" and "b" ("a'" and "b'") and of the center of a reference window 31 (31') provided to surround the bump 1 (1') as shown in FIG. 11A are determined. Note that the bump 1 and the bump 1' are adjacent bumps. Then, with the center coordinates referenced, the reference window 31 (31') is enlarged by changing the coordinates of the corners "a" and "b" ("a'" and "b'") according to the given magnification. As a result, an enlarged window 32 (32') is set so as not to overlap the outline of the associated bump 1 (1') nor the enlarged window 32' (32) for the adjacent bump 1' (1), as shown in FIG. 11B.

Figure 11B:
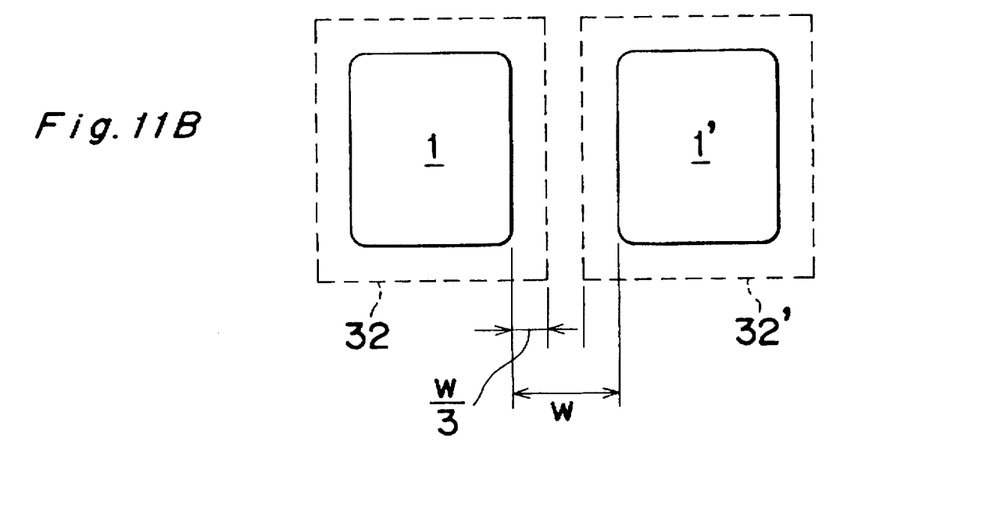
FIG. 11B illustrates reference windows obtained by modifying the windows of FIG. 11A, which are optimum for extracting profiles of bumps.

In FIG. 11B, the enlarged window 32 is so set as to extend outward of the bump 1 by one third of the spacing "w" between the bump 1 and its adjacent bump 1'. Setting the enlarged window 32 in this way allows characteristic values to be easily extracted without losing the characteristics of the outline of the bump 1.

Subsequently, data of the image of the bump 1 surface within the enlarged window 32 set in the above way are thresholded to binary data 1 or 0. Then the coordinates of the pixels at the boundary between the bump 1 and its neighborhood are obtained based on the resulting binary image data. Then, by approximating the shape of the outline of the bump 1 into a simple form from the coordinates of the boundary pixels, a deviation of the approximated shape from the outline shape of a good bump is calculated and taken as a characteristic value of the defect. The value of the deviation is then compared with a predetermined evaluation value. Whether or not the bump 1 inspected is defective in shape is discriminated based on the comparison result.

As described above, in this embodiment, after placed on the stage 11 of the bump appearance inspection apparatus, the wafer 3 is aligned under bright field illumination by a light beam from the light source 8. Thereafter, the wafer 3 is illuminated by the ring light with dark field illumination. Image data of the bump image obtained by the CCD 10 under dark field illumination are stored in the image memory. Then by setting optimal windows created by modifying the reference window by the image processor 15, characteristic values are extracted. Subsequently, in view of the fact that adjacent bumps are similar in their surface state because of their equal formation conditions, a statistical processing is carried out on the above extracted characteristic values of a plurality of bumps according to the equations (1) through (3) to evaluate whether the bumps are defective or not.

Consequently, according to this embodiment, it is possible to permit variation in characteristic values of good bumps within an arbitrary range by performing the statistical processing as described above. It is also possible to distinguish defective bumps while permitting effects of surface roughness such as probe traces within a certain range.

In this connection, since the bump 1 grows isotropically during the bump formation process, a correlation holds between the height and width of the bump 1. Taking advantage of this fact, the height of the bump 1 is obtained from its width.

Therefore, according to this embodiment, any bump height faults can be easily detected from images of the bump surface.

Further, in selecting candidates for defective bump by extracting characteristic values (an average value of image density and a standard deviation of image density in this case) from images of the bumps, two subwindows which are formed by longitudinally dividing a window surrounding the low-brightness portion 26 of the bump image, another two subwindows which are formed by laterally dividing the same window, and a subwindow which is provided at the center portion of the low-brightness portion 26, totally five subwindows, are used.

Therefore, according to this embodiment, in capturing slight changes in characteristic values based on the characteristic values extracted from the subwindows, characteristic values even under the divisional lines in the window can be securely extracted.

Further, when the defect "large foam" is detected by quantitatively determining characteristic values within the opening of the bump 1, the following first and second windows 27, 28 formed on the basis of the reduced reference window surrounding the low-brightness portion 26 of the image of the bump surface are formed: the first window 27 wherein a center portion 29 of the reduced reference window is masked, and the second window 28 wherein a peripheral portion of the reduced reference window that corresponds to the region of the first window 27 is masked. Then first and second characteristic values extracted from the first window and from the second window are respectively weighted, before characteristic values of the defect "foam" are obtained therefrom.

Therefore, according to this embodiment, characteristic values of the defect "foam" can be obtained without being affected by the high-brightness portion 25 associated with the upheavals on the periphery of the bump 1 and the protrusions projecting inward to the opening from the upheavals.

Further, an average value of the characteristic values calculated by weighting the first and second characteristic values is calculated, and the resulting average value is compared with an evaluation value. This makes it possible, for example, to distinguish the defect "edge effect" that would occur due to current density abnormality in formation of the bump, from the different defect "foam".

Moreover, in performing the shape inspection on the bump, by enlarging a reference window provided around the high-brightness portion 25 of the surface image of the bump 1, an enlarged window 32 is provided so as to surround the bump 1 but not to overlap the outline of the bump 1 nor an enlarged window 32' for an adjacent bump 1'. Then by approximating the outline of the bump 1 obtained from the image data of the bump 1 within the enlarged window 32 and then determining a deviation of the approximated outline from the outline of a good bump, characteristic values relating to the outline of the bump are obtained. Therefore, according to this embodiment, characteristic values of the outline shape or configuration can be obtained stably based on the image data within the enlarged window 32 that does not overlap the outline of the bump 1 in the image.

The algorithm for the operation of bump appearance inspection processing of the present invention is not limited to that shown in the flow chart of FIG. 4. That is, it is not necessary to perform all the steps S8 through S10 in the flow chart shown in FIG. 4, but those steps may be combined appropriately as required.

Further, although semi-straight type bumps have been taken as an example in the above-described embodiment, the present invention is not limited to those.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A bump appearance inspection method for inspecting appearance of bumps formed at respective pad electrodes on a semiconductor chip, comprising the steps of:

(a) illuminating a surface of the semiconductor chip with the bumps at a given angle to the surface of the semiconductor chip from all sides of the semiconductor chip;

(b) capturing an image of the surface of the semiconductor chip with the bumps using light reflected by the surface;

(c) storing image data of the captured image in an image memory;

(d) defining for each bump a reference window along an outer edge of the bump in the image;

(e) recognizing for each bump based on the image data a higher brightness, ring-shaped bump region at a periphery of the bump and a lower brightness bump region at a center of the bump enclosed by the higher brightness, ring-shaped bump region;

(f) defining for each bump a new window within the reference window on the basis of a boundary between the higher brightness bump region and the lower brightness bump region;

(g) extracting the characteristic value of each bump from the image data within the new window;

(h) obtaining an evaluation value having a permissible range for the new window based on an average value and a dispersion value determined using of the characteristic values of the bumps within the respective new windows;

(i) comparing the characteristic value of each bump within the new window with the evaluation value for the new window; and (j) considering the bump to be a defective bump when the comparison result indicates that the characteristic value of the bump is outside of the range of the evaluation value.

2. The bump appearance inspection method according to claim 1, wherein the step (f) comprises the substeps of:

defining a lower brightness window which defines an inner edge of the ring-shape of the higher brightness bump region and which surrounds the center region of the bump; and dividing the lower brightness window into a plurality of subwindows each of which serves as the new window wherein the characteristic values in the image are extracted from the subwindows, and wherein the evaluation value for each new window is calculated from the characteristic values extracted from the image data within the subwindows located at same positions in the respective lower brightness windows for the bumps such that effects of flaws or surface roughness of the lower brightness region of each bump are permitted within a certain range.

3. The bump appearance inspection method according to claim 2, further comprising the steps of:

selecting, as candidates for a defective bump, bumps considered to be defective bumps at the step (j);

defining the subwindows to include a first subwindow formed by masking a center portion of the lower brightness window and a second subwindow occupying the center portion of the lower brightness window;

thresholding the image data within the first and second subwindows into binary image data;

extracting a first characteristic value from the binary image data within the first subwindow and a second characteristic value from the binary image data within the second window for each defective bump candidate;

calculating a characteristic value of each defective bump candidate attributable to a defect in the recess portions of the bumps, using the extracted first and second characteristic values;

obtaining an evaluation through statistical processing of the characteristic values of the defective bump candidates, the evaluation value having a permissible range;

comparing the characteristic value of each defective bump candidate with the evaluation value; and determining that the defective bump candidate is a defective bump when its characteristic value is outside of the permissible range of the evaluation value, wherein a defect in the recess portion of the bump is detected without detecting as a defect an effect of surface roughness or a shape of the bump within a certain range.

4. The bump appearance inspection method according to claim 3, further comprising the steps of:
   calculating an average value of the obtained characteristic values of the defective bump candidates;
   comparing the calculated average value with a predetermined evaluation value; and
   deciding, when the average value exceeds the evaluation value, that a plurality of bumps are defective,
   wherein an abnormal peripheral edge upheaval effecting a plurality of bumps due to a current density abnormality during bump formation is detected.

5. The bump appearance inspection method according to claim 2, further comprising the steps of:
   selecting, as candidates for a defective bump, bumps considered to be defective bumps at the step (j);
   thresholding the image data of each defective bump candidate into binary image data and extracting the lower brightness region from the binary image data to obtain an outline of the lower brightness region;
   calculating a characteristic value indicative of a shape of the lower brightness region based on the outline obtained;
   comparing the calculated characteristic value with a predetermined evaluation value; and
   deciding, when the characteristic value exceeds the evaluation value, that the defective bump candidate is a defective bump,
   wherein a defective recess in a peripheral portion of the bump is detected.

6. The bump appearance inspection method according to claim 3, further comprising the steps of:
   thresholding the image data of each defective bump candidate into binary image data and extracting the lower brightness region from the binary image data to obtain an outline of the lower brightness region;
   calculating a characteristic value indicative of a shape of the lower brightness region based on the outline obtained;
   comparing the calculated characteristic value with a predetermined evaluation value; and
   deciding, when the characteristic value exceeds the evaluation value, that the defective bump candidate is a defective bump,
   wherein a defective recess in a peripheral portion of the bump is detected.

7. The bump appearance inspection method according to claim 4, further comprising the steps of: selecting, as candidates for a defective bump, bumps considered to be bumps at the step (j);
   thresholding the image data of each defective bump candidate into binary image data and extracting the lower brightness region from the binary image data to obtain an outline of the lower brightness region;
   calculating a characteristic value indicative of a shape of the lower brightness region based on the outline obtained;
   comparing the calculated characteristic value with a predetermined evaluation value; and
   deciding, when the characteristic value exceeds the evaluation value, that the defective bump candidate is a defective bump,
   wherein a defective recess in a peripheral portion of the bump is detected.

8. The bump appearance inspection method of claim 2, further comprising the steps of:
   selecting, as candidates for a defective bump, bumps considered to be bumps at the step (j);
   enlarging the reference window for each candidate at a given magnification;
   thresholding the image data of each defective bump candidate within the enlarged reference window into binary image data;
   extracting the higher brightness region corresponding to the peripheral portion of the defective bump candidate from the binary image data to obtain an outline of the higher brightness region;
   calculating a characteristic value indicative of a shape of the higher brightness region based on the outline obtained;
   comparing the calculated characteristic value with a predetermined evaluation value; and
   deciding, when the characteristic value exceeds the evaluation value, that the defective bump candidate is a defective bump,
   wherein an abnormal shape of the bump is detected.

9. The bump appearance inspection method of claim 3, further comprising the steps of:
   selecting, as candidates for a defective bump, bumps considered to be defective bumps at the step (j);
   enlarging the reference window for each defective bump candidate at a given magnification;
   thresholding the image data of each defective bump candidate within the enlarged reference window into binary image data;
   extracting the higher brightness region corresponding to the peripheral portion of the defective bump candidate from the binary image data to obtain an outline of the higher brightness region;
   calculating a characteristic value indicative of a shape of the higher brightness region based on the outline obtained;
   comparing the calculated characteristic value with a predetermined evaluation value; and
   deciding, when the characteristic value exceeds the evaluation value, that the defective bump candidate is a defective bump,
   wherein an abnormal shape of the bump is detected.

10. The bump appearance inspection method of claim 4, further comprising the steps of:
    selecting, as candidates for a defective bump, bumps considered to be defective bumps at the step (j);
    enlarging the reference window for each candidate at a given magnification;
    thresholding the image data of each candidate within the enlarged reference window into binary image data;
    extracting the higher brightness region corresponding to the peripheral portion of the candidate from the binary image data to obtain an outline of the higher brightness region;
    calculating a characteristic value indicative of a shape of the higher brightness region based on the outline obtained;
    comparing the calculated characteristic value with a predetermined evaluation value; and
    deciding, when the characteristic value exceeds the evaluation value, that the defective bump candidate is a defective bump, wherein an abnormal shape of the bump is detected.

11. The bump appearance inspection method of claim 5, further comprising the steps of:
- selecting, as candidates for a defective bump, bumps considered to be defective bumps at the step (j);
- enlarging the reference window for each defective bump candidate at a given magnification;
- thresholding the image data of each defective bump candidate within the enlarged reference window into binary image data;
- extracting the higher brightness region corresponding to the peripheral portion of the candidate from the binary image data to obtain an outline of the higher brightness region;
- calculating a characteristic value indicative of a shape of the higher brightness region based on the outline obtained;
- comparing the calculated characteristic value with a predetermined evaluation value; and
- deciding, when the characteristic value exceeds the evaluation value, that the defective bump candidate is a defective bump, wherein an abnormal shape of the bump is detected.

12. The bump appearance inspection method of claim 6, further comprising the steps of:
- selecting, as candidates for a defective bump, bumps considered to be defective bumps at the step (j);
- enlarging the reference window for each defective bump candidate at a given magnification;
- thresholding the image data of each candidate within the enlarged reference window into binary image data;
- extracting the higher brightness region corresponding to the peripheral portion of the candidate from the binary image data to obtain an outline of the higher brightness region;
- calculating a characteristic value indicative of a shape of the higher brightness region based on the outline obtained;
- comparing the calculated characteristic value with a predetermined evaluation value; and
- deciding, when the characteristic value exceeds the evaluation value, that the defective bump candidate is a defective bump, wherein an abnormal shape of the bump is detected.

13. The bump appearance inspection method of claim 7, further comprising the steps of:
- selecting, as candidates for a defective bump, bumps considered to be defective bumps at the step (j);
- enlarging the reference window for each defective bump candidate at a given magnification;
- thresholding the image data of each defective bump candidate within the enlarged reference window into binary image data;
- extracting the higher brightness region corresponding to the peripheral portion of the candidate from the binary image data to obtain an outline of the higher brightness region;
- calculating a characteristic value indicative of a shape of the higher brightness region based on the outline obtained;
- comparing the calculated characteristic value with a predetermined evaluation value; and
- deciding, when the characteristic value exceeds the evaluation value, that the defective bump candidate is a defective bump, wherein an abnormal shape of the bump is detected.

14. The bump appearance inspection method according to claim 1, further comprising the steps of:
- thresholding image data of each bump within the reference window into binary image data;
- determining a width of each bump based on the binary image data;
- calculating a height of the bump based on the width of the bump;
- calculating an evaluation value with a permissible range through application of a statistical processing to the heights of the bumps;
- comparing the height of each bump with the evaluation value; and
- determining that the bump is defective with respect to its height when a value of the height is outside of the range of the evaluation value.

15. A bump appearance inspection apparatus for detecting defective bumps, comprising:
- a support for supporting a semiconductor chip with bumps formed at its respective pad electrode sites;
- image capture means for capturing an image of a surface of the semiconductor chip with the bumps using light reflected by the surface;
- a drive for moving the support such that the bumps of the semiconductor chip on the support are positioned directly below the image capture means;
- illumination for illuminating the surface of the semiconductor chip with the bumps at a given angle to the surface of the semiconductor chip from its entire periphery;
- a memory for storing image data of the image captured by the capture means;
- data process circuitry for performing the following tasks:
- defining a reference window along an outer edge of each bump in the image recognizing for each bump based on the image data a higher brightness, ring-shaped bump region at a periphery of the bump and a lower brightness bump region at a center of the bump enclosed by the higher brightness, ring-shaped bump region, wherein the higher brightness, ring-shaped region in the image corresponds to a peripheral, protruded portion of the bump and the low brightness bump region in the image corresponds to a recess portion of the bump;
- defining a new window within the reference window according to a surface state of the bump so that characteristic values of the bumps attributable to a defect in the recess portion can be accurately extracted;
- extracting the characteristic values of the bumps attributable to the defect from the image data within the new window;
- calculating an obtaining value having a permissible range based on an average value and a dispersion value calculated using the extracted characteristic values of the bumps; and
- comparing the characteristic value of each bump with the calculated evaluation value and discriminating based on the comparison result whether the bump is defective or not and deciding that the bump is a defective bump when its characteristic value is outside of the permissible range.

* * * * *

UNITED STATES PATENT AND TRADEMARK OFFICE
CERTIFICATE OF CORRECTION

PATENT NO. : 5,761,337
DATED : June 2, 1998
INVENTOR(S) : Nishimura, et al.

It is certified that error appears in the above-identified patent and that said Letters Patent is hereby corrected as shown below:

Column 22, line 56, delete "calculating an" and after "obtaining" insert --an evaluation--.

Column 22, line 61, delete "calculated".

Signed and Sealed this

Sixteenth Day of March, 1999

Attest:

Q. TODD DICKINSON

*Attesting Officer*    *Acting Commissioner of Patents and Trademarks*